United States Patent [19]

Seib et al.

[11] Patent Number: 4,647,672

[45] Date of Patent: Mar. 3, 1987

[54] ASCORBATE 2-POLYPHOSPHATE ESTERS AND METHOD OF MAKING SAME

[75] Inventors: Paul A. Seib; Ming-Long Liao, both of Manhattan, Kans.

[73] Assignee: Kansas State University Research Foundation, Manhattan, Kans.

[21] Appl. No.: 749,081

[22] Filed: Jun. 25, 1985

[51] Int. Cl.$^4$ ............................................... C07F 9/09
[52] U.S. Cl. .................................................. 549/222
[58] Field of Search ........................................ 549/222

[56] References Cited

U.S. PATENT DOCUMENTS 4,179,445 12/1979 Seib et al. ...................... 549/222 X

OTHER PUBLICATIONS

Nomura et al, Chemical Abstracts, vol. 74 (1971), 31939v.

Primary Examiner—Richard L. Raymond
Attorney, Agent, or Firm—Schmidt, Johnson, Hovey & Williams

[57] ABSTRACT

A new stable derivative of ascorbic acid, ascorbate 2-polyphosphate, is disclosed, together with a high-yield method of synthesis thereof. The method preferably includes steps of reacting an ascorbic acid such as L-ascorbic acid or a derivative thereof such as 5,6-O-isopropylidene-L-ascorbic acid with salts of metaphosphoric acid in an aqueous system and in the presence of sufficient base to maintain the pH of the reaction mixture at a level of at least above 9 to obtain 2-polyphosphorylation of the ascorbic acid. In particularly preferred forms, 1 M L-ascorbic acid is reacted in water with 1.5-3 equivalent of sodium or potassium trimetaphosphate at a temperature of 25°-55° C., and an alkali metal hydroxide such as potassium hydroxide is intermittently added to the reaction mixture as needed over a 1-10 hr. reaction period to maintain the pH thereof at a level of about 10.5-12 during the entire reaction. After neutralization the reaction mixture contains no noxious or toxic materials, and the entire mixture may be added to food or feed. Pure salts of ascorbate 2-triphosphate can be isolated readily using conventional chromatographic techniques. It has also been found that the compounds of the invention are more difficult to oxidize, and release ascorbic acid and are more slowly hydrolyzed than the monophosphate derivative of ascorbic acid.

21 Claims, 1 Drawing Figure

ASCORBATE 2-POLYPHOSPHATE ESTERS AND METHOD OF MAKING SAME

BACKGROUND OF THE INVENTION

1. Field of the Invention

The present invention is concerned with novel ascorbate 2-polyphosphate esters, as well as methods for the synthesis of such esters and the corresponding salts thereof. More particularly, it is concerned with L-ascorbate 2-triphosphate which has been shown to be a new stable form of vitamin C, and which can be prepared and recovered at lower cost than prior stable forms of vitamin C such as the monophosphate form, L-ascorbate 2-phosphate.

2. Description of the Prior Art

L-Ascorbic acid and D-isoascorbic acid are two stereoisomeric six-carbon ascorbic acids that have many uses in pharmaceuticals, food, feed, and a variety of minor products. The utility of L-ascorbic acid arises mainly from its vitamin C activity, strong reducing power, and low toxicity, while the use of D-isoascorbic acid depends on its strong reducing power and its low cost compared to L-ascorbic acid. The use of D-isoascorbic acid in foods and feeds is restricted because of its low vitamin C activity and its antagonist effect on the absorption of L-ascorbic acid in the digestive tract. Because L-ascorbic acid reduces oxygen, the vitamin is often lost as it contacts air during processing and storage of food and feed. On long term storage in an acid medium, especially under heat, L-ascorbic acid is also destroyed by a second process involving dehydration of the molecule. Thus, nutritionists and food scientists have long sought a form of vitamin C that is stable to air and acid, prticularly to air.

Two methods have been used in the past to increase the stability of ascorbic acid, encapsulating the solid crystals of L-ascorbic acid, and chemically substituting the ene-diol functional group on the molecule. Fat-encapsulated forms of vitamin C have several shortcomings. The larger the crystals of L-ascorbic acid that are coated, the more difficult it is to distribute the coated vitamin in a food or feed, especially if the food or feed is finely divided. On the other hand, the smaller the crystals of L-ascorbic acid, the less perfect the en-capsulation. Typically, crystals of 250–300 micrometers (50–60 mesh) are coated with 15–50% add-on fat. During processing of food or feed, the protective fat coating may be melted away or rubbed off the crystals. Encapsultated particles are coated with triglycerides that melt at 50°–60° C.; or with wax such as caranauba, which melts at about 85° C. It is likely that caranauba coated L-ascorbic acid is not digestible, and is therefore unavailable to animals. L-Ascorbic acid has also been encapsultaed with polymers that slowly dissolve to release vitamin C. During processing of food or feeds, these types of coated forms may give substantial losses of the vitamin.

Chemically modified forms of L-ascorbic acid circumvent the problems of stability, particlesize, and biological availability of coated forms. The chemically modified forms are stabilized against oxygen by substituting of the 2- or 3-hydroxyl of L-ascorbic acid. Examples of these derivatives include the 2- or 3-methyl ethers, the 2-sulfate ester, the 2-phosphate ester, and the 2,2-bis-(L-ascorbyl) phosphate ester. Of these examples, the 2-phosphate ester of L-ascorbic acid has been shown to be an active form of vitamin C in monkeys, and presumably in other primates such s man (L. J. Machlin et al, *Am. J. Clin. Nutr.* 32, 1979, p 325). The 2-sulfate ester is not an active source of vitamin C in guinea pigs and monkeys, (L. J. Machlin, *Am. J. Clin. Nutr.* 29, 1976, p 825), but it is in fish and possibly crustacea (J. E. Halver et al, *N.Y. Acad. Sci.* 258, 1975, p 81). The methyl esters are only about 5% active in guinea pigs (P. W. Lu et al, *J. Ag. Food. Chem.* 32, 1984, p 21).

L-Ascorbate 2-phosphate (ASMP) has been known since 1961 when it was first reported by Italian workers (E. Cutolo and A. Larizza, *Gazz. Chim. Ital.* 91, 1961, p 964). Other investigators have since improved the chemical synthesis of L-ascorbate 2-phosphate so that 86% of the magnesium salt can be isolated in almost pure form without chromatrographic purification starting form L-ascorbic acid (P. A. Seib et al. U.S. Pat. No. 4,179,445, Dec. 18, 1979). Methods to prepare 2,2'-bis-(L-ascorbyl) phosphate are moderately successful (about 30% yield, C. H. Lee, et al, *Carbohydrate Res.* 67, 1978, p 127), but the vitamin C activity of the diascorbyl phosphate is unknown.

L-Ascorbate 2-pyrophosphate (L-ascorbate 2-diphosphate) has been prepared by reaction of phosphorus oxychloride with 5,6-O-isopropylidene-L-ascorbic in a mixture of water, acetone and pyridine (H. Nomura et al., *Chem. Phar. Bull.*, Japan, 17, 1969, 381). The pyrophosphate ester was obtained in only 5% yield, and it had to purified from three other reaction products using ion-exchange chromatography. The low yield and difficult purification renders L-ascorbate 2-pyrophosphate an impractical source of stable vitamin C for commercial purposes.

SUMMARY OF THE INVENTION

The present invention resides in part in the discovery of a new stable form of ascorbic acid, namely ascorbate 2-polyphosphate (ASPP) and the corresponding salts thereof (e.g., alkali metal or ammonium, although virtually any desired salt-forming cation may be used). ASPP has the generalized formula:

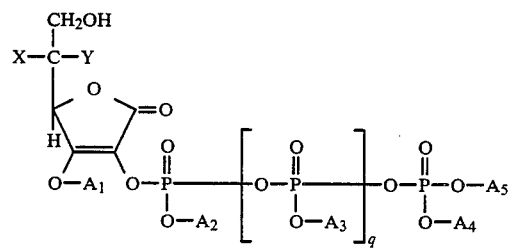

where X and Y are different respectively taken from the group consisting of —H and —OH, and q normally ranges from 1 to 4; in addition $A_1$, $A_2$, $A_3$, $A_4$ and $A_5$ are respectively taken from the group consisting of hydrogen and salt-forming cations.

One particularly preferred example of a new composition in accordance with the invention is L-ascorbate 2-triphosphate, which in the ionized form has the formula:

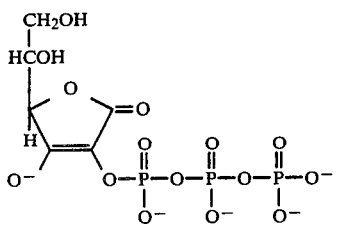

II

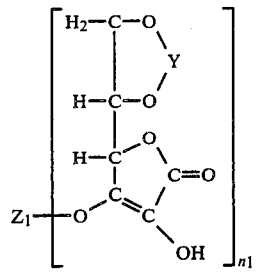

IV

Broadly speaking, the synthesis of the ascorbate 2-polyphosphate of the invention involves forming a reaction mixture comprising respective quantities of ascorbic acid or a derivative thereof, a water soluble salt of metaphosphoric acid, water, and sufficient base to give the mixture a pH of at least about 9. This mixture is then allowed to react for a period of time to allow the polyphosphorylation reaction to proceed (e.g., from 1 to 24 hours, or more preferably for 1 to 12 hours). During this reaction, however, the pH of the reaction mixture is maintained above about 9, usually by periodic addition of base. The polyphosphorylated product can be used directly, or edible salts thereof may readily be recovered using column chromatography.

In the most preferred emthod, L-ascorbate 2-triphosphate (ASTP) is produced by reacting L-ascorbic acid (initially a 1 molar solution) with two equivalents of sodium trimetaphosphate in water at 32°–35° in the presence of potassium or sodium hydroxide sufficient to maintain the pH of the reaction mixture at a level of 10.5 to 12 during the entire reaction period.

In more detail, the ascorbic acid compound is preferably selected from the group consisting of ascorbic acid, the alkali and alkaline earth metal salts of ascorbic acid, the tertiary amine salts of ascorbic acid, and derivatives of ascorbic acid having a $C_6$ base-stable blocking group thereon. Examples of the latter type of compound are the 5,6-acetal and 5,6-ketal derivatives of ascorbic acid, such as 5,6-O-benzylidiene-L-ascorbic acid and 5,6-O-isopropylidene-L-ascorbic acid. In the most preferred form of the invention, the ascorbic acid reactant is selected from the group consisting of the four stereoisomers of the compound with the forumla

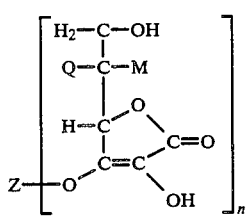

III where Z is selected from the group consisting of hydrogen, the alkali metals, the alkaline earth metals and the tertiary amines, n is the valence of Z, and Q and M are different and taken from the group consisting of —H and —OH and compounds of the formula wherein $Z_1$ is selected from the group consisting of hydrogen, the alkali metals, alkaline earth metals and the tertiary amines, $n_1$ is the valence of $Z_1$ and Y represents cycloalkyls having from 5 to 7 carbon atoms or a group of the formula

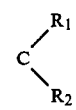

V where $R_1$ represents hydrogen, phenyl, furfural or alkyl groups of from 1 to 4 carbon atoms, and $R_2$ represents hydrogen or alkyl groups of from 1 to 4 carbon atoms.

The phosphorylating agent is a salt of metaphosphoric acid, $M_x(PO_3^-)_y$, which is a cyclic polyphosphate anion with a negative charge y, a ring-size of 2y atoms, and $M_x$ is a metal ion whose cationic charge neutralizes the negative charge of the phosphate. When $y=3$, the phosphorylating agent is the readily available trimetaphosphate, i.e.:

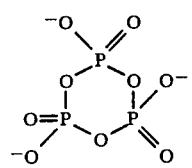

Other individual species of metaphosphate salts include tetra-, penta-, and hexametaphosphate salts. A large number of mixed metaphosphates are possible. The most preferred salts are the alkali metal salts, such as sodium or potassium metaphosphate, although other salts can be employed.

The reactants are preferably mixed in an aqueous solvent that does not interfere with the desired polyphosphorylation reaction. Water is the most preferred reaction medium. Sufficient base is added, preferably in an intermittent fashion during the reaction, to maintain the reaction mixture at a pH of at least about 9 during the entire reaction between the components. If the pH is too low, the rate of formation of ASPP is slow, while if the pH is too high (greater than about 13), then highly concentrated hydroxide ions react with the metaphosphate reagent in preference to reaction with ascorbate. Thus, very high basicity destroys the phosphorylating reagent. Furthermore, at pH greater than about 12, a by-product begins to accumulate in the reaction mixture as indicated by an extra absorption band at 313 nm in the ultraviolet (uv) spectrum of the final reaction mixture. Below pH 12, the uv spectrum of the final reaction product is essentially a single absorption band with an absorption maximum at 258 nm. For these reasons then, the more preferred reaction pH levels are from about 10 to 12.5, and most preferably from about 10.5 to 12 in the case of triphosphorylation.

The base added to the reaction mixture should be substantially miscible therein, of suitable base strength to achieve the desired reaction pH, and should not cause precipitation of the metaphosphate reagent. Bases consisting of the alkali metal hydroxides are preferred.

To enhance the production of ASPP the concentration of reagents should be controlled to a certain extent. When pH is controlled by sodium or potassium hydroxide the initial concentration of ascorbic acid or its derivative IV should be from about 0.5 to 4M, while the molar ratio of metaphosphate to ascorbate should be approximately 1.5 to 3. In the most preferred process to prepare ASTP, those ranges should be 0.75 to 1.5M with a molar ratio of 1.5 to 3.

The upper temperature limit of the reaction is chosen to minimize loss of ascorbic acid during the reaction, to minimize the by-product with uv absorbance at 313 nm, and to maximize the uv absorbance of the desired ASPP at 258 nm. The lower temperature limit is dictated by the length of reaction period needed to achieve high conversion of ascorbate to the phosphate ester. Broadly, to produce L-ascorbate 2-triphosphate the temperature range is 20° to 80° C., with the preferred range of 25°–55°. To produce 2-phosphorylated ascorbic acid from a higher molecular weight metaphosphate than the trimetaphosphate, the temperature used increases somewhat with the molecular size of the metaphosphate. For example, with hexametaphosphate the reaction temperature is 50°–80° C. The reaction is usually carried out with the exclusion of air to avoid oxidative destruction of the starting ascorbic acid.

The reaction period needed to achieve high yields of ASPP depends on temperature, pH and the concentration of reactants. High pH, high temperature and high concentration of reactants favor short reaction periods. For example, when 1.0M L-ascorbic acid is reacted with 2.0M sodium trimetaphosphate at pH of about 11 at 55°, virtually all L-ascorbic acid is reacted in 1 hour. Using the same conditions, except adjusting the temperature to 33° C., 8 hrs. was required to react all L-ascorbate. When 1M ascorbic acid was reacted with 2M trimetaphosphate at 35° and pH about 11 or about 10, after 8 hrs., 93% and 33%, respectively, 2-phosphorylation was observed.

After the polyphosphorylation reaction has been completed, the reaction pH is adjusted to pH 3–8, or more preferably to pH 7, with an edible mineral or organic acid. The aqueous reaction mixture contains no noxious solvents or reagents, but instead contains mineral nutrients and, in the case of polyphosphate esters of L-ascorbic acid, vitamin C activity as well. A very small amount of ascorbic acid is caramelized at the alkaline pH of the reaction mixture, which gives a pleasant odor and a light yellow color. Thus, it is believed that the entire reaction mixture can be added to food or feed, with or without removal of the reaction water prior to nutrification.

If ascorbate 2-polyphosphate is desired free of inorganic phosphate salts, separation and purification can be readily achieved using ion-exchange column chromatography. For example, in the case of ASTP, the reaction mixture may be adjusted to pH 8.5 by stirring with a strongly acidic cation-exchange resin in the hydrogen-ion form. The cation-exchange resin is removed quickly by filtration, and the mixture is added to the top of a column of strongly basic anion-exchange resin in the bicarbonate form. Elution with 0.4M ammonium bicarbonate removes inorganic phosphates, and elution with 0.5M ammonium bicarbonate elutes pure ascorbate 2-triphosphate. Evaporation of the column effluent removes most of the water and all the ammonium bicarbonate. Salts of ASTP with any desirable cation can then be made by passage of the residual ammonium salt of ASTP through a cation exchange resin in the cation form of choice. Purification of ASTP could also be achieved using charcoal column chromatography as described by Takeda Chem. Industries, *Jpn. Kokai Tokkyo Koho,* JP No. 59 36, 539 (*Chem. Abst.* 101, 1984, 10695p).

To purify other 2-polyphosphate esters of ascorbate besides ASTP, it may be necessary to adjust the concentration of eluting salt and base solutions compared to those used for ASTP.

The 2-polyphosphate esters of ascorbic acid can be used to produce the 2-monophosphate ester. In acid at pH 0–1, the linear phosphate chain on an ascorbate 2-polyphosphate is hydrolyzed preferentially between phosphoryl residues rather than between the 0–2 position on ascorbate, and the 2-phosphoryl residue. The triphosphate ester is hydrolyzed to predominately L-ascorbate 2-phosphate and some L-ascorbic acid.

As indicated, the principal utility for the compounds of the invention is as a stable source of vitamin C which is resistant to oxidation and acidic or enzymatic hydrolysis. The products hereof obtained by reaction of L-ascorbic acid may be used as additives in food or feeds, or in pharmacological applications. Products obtained by reaction of D-isoascorbic acid may be used in admixture with controlled amounts of phosphatase enzyme to provide a sustained supply of reducing power.

Surprisingly, it has been found ASTP is more stable to oxidation than ASMP. Furthermore, L-ascorbate is stabilized against autoxidation by ASTP in aqueous medium at pH 7, probably due to the ability of ASTP to chelate divalent mineral ions, such as copper and iron. As such, the new compounds of the invention exhibit enhanced stability properties as compared with the prior monophosphate derivative.

The lowest member of the 2-polyphosphate esters of L-ascorbate prepared by the present invention is the 2-triphosphate ester, which resembles adenosine triphosphate (ATP). ATP is present in all cells; it is the chemical storage form of energy, and it participates in innumerable biochemical reactions in living organisms. It is possible, therefore, that ASTP might find medical uses, if ASTP antagonizes the function of ATP in biochemical transformations.

The 2-triphosphate ester of L-ascorbic acid is an active form of vitamin C in guinea pigs, (see FIG. 1), and almost certainly in all other animals. Phosphatase enzymes are present in the digestive tract of all animals, and that enzyme removes three phosphate residues from ASTP in stepwise fashion until L-ascorbic acid is released. The stepwise removal of phosphate residues from adenosine triphosphate (ATP) with the release of adenosine and inorganic phosphate by phosphatase has been demonstrated a number of times (D. L. M. Verheydes et al, *J. Am. Chem. Soc.* 87, 1965, p 2257, and L. A. Heppel et al, *J. Biol. Chem.* 237, 1962, p 841). Thus, it is anticipated that ASTP will find uses in foods and feeds, both for nutritional and probably functional purposes. ASTP, like ASMP, might also be used to stabilize whole blood (G. L. Moore et al., *Transfusion* 21, 1981, p 723).

Three separate hydrolytic steps are required to release L-ascorbate from ASTP vs only one step for such release from ascorbate monophosphate ASMP. It is therefore theorized that the enhanced hydrolytic stability of ASTP as compared to ASMP can be explained by this factor. However, the enhanced oxidative stability of ASTP vs ASMP is surprising, as shown in Table III. ASMP is completely destroyed by hydrogen peroxide oxidation, while under the same condition 55% ASTP remains. In any event, it is believed that ASTP and other ASPP esters can provide a stable source of vitamin C in foods and feed in which ASMP is acid-or-enzyme-hydrolyzed to L-ascorbic acid with consequent loss of vitamin C activity. In other systems containing limited amounts of phosphatase, a mixture of ASMP and ASPP could provide a slow and sustained release of L-ascorbic acid over a period of time longer than an equivalent amount of ASMP alone. In some systems, the phosphate released by enzymic hydrolysis of ASPP may be high enough to competitively inhibit the phosphatase enzyme so that loss of the 2-phosphorylated derivative would diminish, and give a very slow rate of release of ascorbic acid. The oxidative loss of vitamin C in foods and feeds containing ASPP would also be expected to be slow compared to those containing ASMP.

The single FIGURE is a plot of a guinea pig feeding study undertaken to confirm the vitamin C activity of a preferred compound in accordance with the invention, namely L-ascorbate 2-triphosphate.

DESCRIPTION OF THE PREFERRED EMBODIMENTS

Figure 1:
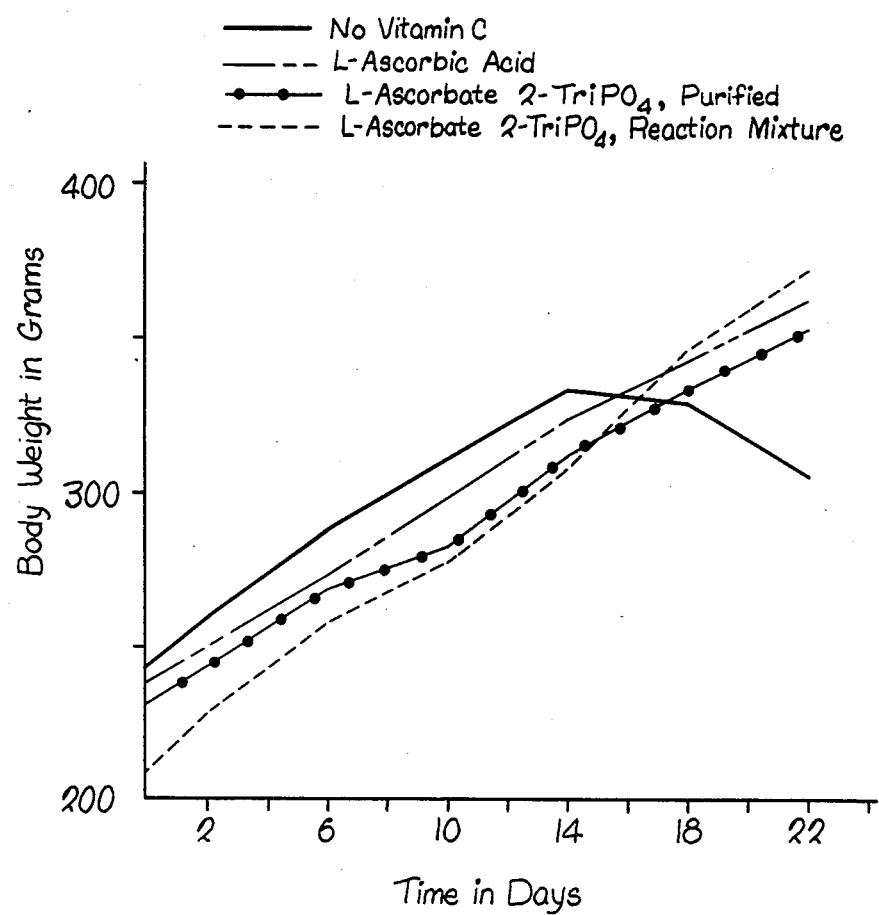

The following examples set forth the most preferred syntheses for the compounds of the invention. It is to be understood, however, that these examples are merely illustrative of the invention and should not therefore be read in a limiting sense.

EXAMPLE I

A 250 ml beaker was fitted with a pH electrode, a magnetic stirring-bar, a nitrogen-inlet tube, and a buret. To the beaker, which was placed in a water bath at 33°-35° C., was added, in sequence, water (55 ml), L-ascorbic acid (10 g, 57 mmole, 1.03M) and 10M potassium hydroxide to pH about 11.0. Sodium or potassium trimetaphosphate (95-97% pure, about 114 mmole) was added, the reaction mixture continuously purged with nitrogen, and the pH maintained at 10.9-11.2 by periodic addition of 10M potassium hydroxide. The reaction mixture was stirred continuously and stopped after 8 hr. reaction time. The reaction mixture, which had a total volume of about 100 ml, was diluted to volume (250 ml.) with water, and an aliquot (5.0 ml.) was titrated immediately with 0.05N aqueous iodine. The iodine titer (2.82 ml.) indicated 6.2% unreacted L-ascorbate. A second aliquot (2.0 ml.) of the diluted reaction mixture was diluted further (6250-fold) in 0.01M sodium carbonate buffer at pH 10. The diluted mixture at pH 10 was allowed to stand 2 hr., during which time L-ascorbate was destroyed by $O_2$-oxidation as shown by uv assay in a separate experiment. In that separate experiment, the reactants were mixed without pH adjustment (which gave pH of about 3), the mixture diluted at pH 10, and the absorbance read at 258 nm and pH 10 was 0.004 after 2 hr. standing. After the diluted triphosphorylation reaction mixture at pH 10 stood 2 hrs., uv absorbance at 258 nm was 0.537, indicating 92.3% 2-phosphorylation of L-ascorbate (assuming $\epsilon_{mM}$ 16 at pH at ph 10 for 2-phosphorylated esters, see Lee et al *Carbohydrate Res.* 67,1978, p 127). The ratio of uv absorbance at 313 nm to 258 nm was 0.014, indicating a very small amount of by-product in the reaction mixture.

Phosphoric acid or hydrochloric acid was next added to the reaction mixture to pH 7.0, and the mixture was evaporated to a light yellow solid. Alternatively, L-ascorbate 2-triphosphate (ASTP) was isolated in pure form by column chromatography. The pH of the reaction mixture (final volume about 100 ml) was adjusted to pH 8.5 by addition of a strongly acidic cation-exchange resin ($H^+$-form), the resin removed, and the mixture then diluted to 250 ml. An aliquot (40 ml) was placed on a column (5×40 cm, 200-400 mesh) of strongly basic anion-exchange resin in the bicarbonate form. Inorganic phosphate salts, detected by molybdate reagent, were eluted first with 0.4M ammonium bicarbonate at a flow rate of 1-2 ml/min. Then, ascorbate 2-triphosphate, detected by uv absorbance at 258 nm, was eluted with 0.5M ammonium bicarbonate. After combining fractions, the solutions were evaporated to dryness, and water was added twice and the mixture re-evaporated. The syrupy ammonium salt of ASTP was dissolved in water, passed through a strongly acidic cation-exchange resin in the sodium-form, and the column effluent evaporated to an amorphous solid. The sodium salt gave the correct elemental analysis, $^{31}P$, $^1H$ and $^{13}C$-nmr spectra, and uv properties consistent with sodium L-ascorbate 2-triphosphate.

Analysis. Calculated for $C_6H_7O_{15}P_3Na_4.2H_2O$: C, 13.33; H, 2.04; P, 17.22; and Na 17.04. Found: C, 13.19; H, 1.83; P, 16.73; and Na 17.84.

EXAMPLE II

Another triphosphorylation reaction was conducted as described in Example I, except the starting material was a 5,6-acetal derivative, 5,6-O-isopropylidene-L-ascorbic (12.3 g). Iodine titration indicated about 10% unreacted L-ascorbic acid, and uv absorption at 258 nm indicated 86% 2-triphosphorylation. To remove the isopropylidene blocking group, the diluted reaction mixture (150 ml) was treated with a strongly acidic cation-exchange resin [hydrogen form] to pH 3.0. The resin was removed quickly by filtration, and the progress of the removal of the 5,6-acetal was monitored using thin-layer chromatography. When the acetal hydrolysis was complete, the mixture was adjusted to pH 8.0 using sodium or potassium hydroxide. Isolation of the reaction products was completed as described in Example I.

EXAMPLE III

The triphosphorylation reaction was conducted as described in Example I, except that D-isoascorbic acid was used in place of L-ascorbic acid. The conversion of D-isoascorbic acid to its 2-triphosphate ester was in about 90% yield, and isolation of the product was performed as described in Example I.

EXAMPLE IV

In this experiment, the pH of the triphosphorylation reaction described in Example I was varied. When L-ascorbic acid (10 g) was stirred with sodium trimetaphosphate (36.6 g, 2 equivalents), the pH of the reaction mixture was about 3. After 12 hr. reaction at 35° no phosphorylation occurred as evidenced by iodine titration, uv analysis and thin-layer chromatography. After 10 days stirring, uv assay at 258 nm showed 5% 2-triphosphorylation. When the pH of the reaction mixture was raised and maintained at 10 for 8 hrs. using sodium or potassium hydroxide, iodine titration gave about 65% unreacted L-ascorbic acid while uv absorption at 258 nm indicated about 33% 2-triphosphorylation. When the pH of the reaction mixture was maintained at 12.8–13.1, iodine titration gave 40% unreacted L-ascorbic acid and uv analysis showed 52% 2-triphosphorylation. Furthermore, when the reaction was carried out at pH 12.8–13.1, the ratio of uv absorbance at 313 nm to 258 nm was 0.12, which indicated formation of a by-product in the reaction mixture. When the pH of the reaction mixture was maintained in the most preferred pH range of 10.5–12 using sodium hydroxide, iodine titration showed 5% unreacted L-ascorbic acid and uv analysis 87% 2-triphosphorylation.

EXAMPLE V

The phosphorylation reaction was conducted as in Example I except the concentration of L-ascorbic acid was reduced from 1M to 0.5M. After 8 hr. reaction time, iodine titration gave 32% unreacted L-ascorbate while uv analysis showed 65% 2-triphosphorylation. When the concentration of L-ascorbate was kept at 1M, but the molar equivalents of trimetaphosphate was changed from 2 to 3, the yield of 2-triphosphate did not increase above 93%.

The temperature of the reaction in Example I as also varied from 20° to 80°. At temperatures above about 60°, the yield of 2-triphosphate declines while the ratio of $A_{313\,nm}/A_{258\,nm}$ increased. At 20° C. reaction temperature, the reaction mixture after 8 hr. contained 25% unreacted starting material and 75% 2-triphosphate ester.

It has also been confirmed that behavior of the 2-monophosphate ester of L-ascorbate, ASMP, towards the enzyme phosphatase is different than the behavior of the 2-triphopsphate ester, ASTP. ASMP releases L-ascorbic acid much faster than ASTP when treated with a purified phosphatase from potato (Table I). In addition, ASTP is more resistant to acid-catalyzed release of L-ascorbate than is ASMP (see "blank" reactions in Table I). In pH 5.0 buffer ASTP released no L-ascorbate after 20 hr. compared to about 15% released by ASMP.

TABLE I

Enzymic Hydrolysis of L-Ascorbate 2-Phosphate (ASMP) and L-Ascorbate 2-Triphosphate (ASTP) using Acid Phosphatase from Potato. L-Ascorbate Released (%) during Enzymolysis.[1]

| Reaction Time, h | Substrate | | | |
|---|---|---|---|---|
| | ASMP | | ASTP | |
| | Blank | Phosphatase | Blank | Phosphatase |
| 0.25 | 0 | 9.3 | 0 | 0 |
| 0.50 | 0 | 18.6 | 0 | 0 |
| 1.0 | 0 | 35.5 | 0 | 0 |
| 2.0 | 2.9 | 60.5 | 0 | 0 |
| 3.0 | 4.6 | 77.3 | 0 | 0.4 |
| 4.0 | 4.6 | 88.4 | 0 | 0.8 |
| 8.0 | 8.1 | 100 | 0 | 3.5 |
| 20.0 | 14.5 | 100 | 0 | 8.5 |

[1]Enzymolysis was done at 25° by stirring 200 micromoles of magnesium L-ascorbate 2-phosphate or ammonium L-ascorbate 2-triphosphate in 100 ml of 0.05 M acetate buffer (pH 5.0) containing about 400 mg of bakers' compressed yeast and 2 units of phosphatase (1 unit activity hydrolyzes 1 μmole of p-nitrophenyl phosphate at pH 4.8 and 37°). At a given reaction time, an aliquot (5 ml) was removed, mixed with 5.0 ml of 12% trichloroacetic acid/4% metaphosphoric acid, and the mixture filtered. An aliquot (5 ml) of the filtrate was titrated with 2,6-dichlorophenolindophenol to a pink end-point. Blank solutions contained all reagents except phosphatase.

The much greater stability of ASTP vs ASMP towards phosphatase also was observed in a model food system (Table II). When stirred with a dilute suspension of wheat flour at 25° C., ASMP was comletely hydrolyzed in 1 hr. whereas ASTP required approximately 10–20 hr. for 95% hydrolysis.

TABLE II

Enzymic Hydrolysis of L-Ascorbate 2-Phosphate (ASMP) and L-Ascorbate 2-Triphosphate (ASTP) in the Presence of Wheat Flour. L-Ascorbate Released (%) during Enzymolysis.[1]

| Reaction Time, h | Substrate | | | |
|---|---|---|---|---|
| | ASMP | | ASTP | |
| | Blank | Phosphatase | Blank | Phosphatase |
| 0.25 | 0 | 47.1 | 0 | 0 |
| 0.50 | 0 | 76.2 | 0 | 1.2 |
| 1.0 | 0 | 100 | 0 | 3.5 |
| 2.0 | 2.9 | 100 | 0 | 29.6 |
| 3.0 | 4.6 | 100 | 0 | 65.8 |
| 4.0 | 4.6 | 100 | 0 | 86.9 |
| 5.0 | 5.8 | 100 | 0 | 93.1 |
| 20.0 | 14.5 | 100 | 0 | 95.0 |

[1]Enzymolysis and titration of L-ascorbate released were done as described in the footnote to Table I, except the phosphatase was that present in wheat flour. Two grams of wheat flour was used in the 100 ml enzymolysis reaction mixture.

L-Ascorbate 2-triphosphate is approximately twice as difficult to oxidize as L-ascorbate 2-monophosphate. When ASTP and ASMP were treated under identical conditions (pH 7, 25° C.) with hydrogen peroxide for 8 days, 77% ASTP remained unreacted while 44% ASMP remained. After 14 days oxidation, 0% ASMP remained compared to 55% ASTP. The parent compound, L-ascorbic acid, was destroyed in less than one hour (Table III). Obviously, ASTP will be much more stable in foods and feeds that contain phosphatase enzyme or oxidants, such as oxygen.

TABLE III

Stability (% Remaining) of L-Ascorbate and Its Phosphate Esters When Reacted with Aqueous Hydrogen Peroxide[1].

| Reaction Time | L-Ascorbate Derivative | | |
|---|---|---|---|
| | Parent Compd | ASMP[2] | ASTP[2] |
| 0.25 h | 56.9 | 98.7 | 98.6 |
| 1.0 h | 0 | 97.1 | 98.3 |
| 1 day | 0 | 93.9 | 96.7 |
| 3 day | 0 | 77.7 | 87.6 |
| 6 day | 0 | 64.1 | 83.3 |
| 8 day | 0 | 44.1 | 77.0 |

TABLE III-continued

Stability (% Remaining) of L-Ascorbate and Its Phosphate Esters When Reacted with Aqueous Hydrogen Peroxide[1].

| Reaction Time | L-Ascorbate Derivative | | |
|---|---|---|---|
| | Parent Compd | ASMP[2] | ASTP[2] |
| 14 day | 0 | 0 | 55.2 |

[1]Reaction mixture contained 0.05 mL of 30% aqueous hydrogen peroxide and 200 micromoles of L-ascorbate or its 2-phosphorylated derivative in 100 ml of 0.05 TRIS buffer (pH 7.0). At a given reaction time, an aliquot (1 ml) of a reaction mixture containing the 2-phosphorylated ester was diluted 10 fold with TRIS buffer at pH 7, and the uv absorbance of the mixture read at 258 nm. To follow loss of L-ascorbic acid, an aliquot (1 ml) of the reaction mixture was diluted with 2% metaphosphoric acid, and the uv absorbance read at 245 nm.

[2]ASMP = L-Ascorbate 2-phosphate; ASTP = L-ascorbate 2-triphosphate.

EXAMPLE VI

English short-hair guinea pigs were housed individually in a cage and fed Purina guinea pig ration during a one-week acclimation period. The young pigs (190–250 g) were divided into four groups of 10 animals each. One group was fed a diet devoid of vitamin C (Reid-Briggs guinea pig diet, U.S. Biochemicals, Cleveland, Ohio); the second group received the same diet but supplemented with 5.0 mg of L-ascorbic acid per kg of body weight per day; the third group received 15.4 mg of purified tetrasodium L-ascorbate 2-triphosphate dihydrate (L-ascorbate 2-tri-PO$_4$, purified) per kg of body weight per day; and the fourth group received 15.4 mg of tetra-sodium L-ascorbate 2-triphosphate dihydrate (L-ascorbate 2-tri-PO$_4$, reaction mixture) in admixture with the by-products of the reaction mixture as set forth in Example I, except the small amount of unreacted L-ascorbic acid in the reaction mixture was destroyed by O$_2$-oxidation (the 15.4 mg of tetrasodium L-ascorbate 2-triphosphate dihydrate is equivalent to 5.0 mg of L-ascorbic acid). The vitamin C was administered orally with a calibrated syringe from solutions kept at 5° C., except the L-ascorbic acid solution was prepared fresh daily. The weights of the animals were recorded daily, and the arithmetic means of each group were calculated and compared in the FIGURE.

This test was designed to confirm the vitamin C activity of L-ascorbate-2-triphosphate in guinea pigs.

The vitamin C activity of ASTP is evident from curves seen in FIG. 1. L-Ascorbate 2-triphosphate was fed to the animals either in pure form (curve labeled L-ascorbate 2-tri-PO$_4$, purified) or in admixture with all the products of the triphosphoryltion reaction mixture (curve labeled L-ascorbate 2-tri-PO$_4$, reaction mixture). The groups of animals given either form of ASTP grew at a rate equal to that of the group fed an equivalent amount of L-ascorbic acid. However, the group of animals given no supplemental source of vitamin C lost weight and grew poorly beginning on approximately the 14th day of the feeding experiment. The animals fed ASTP as a source of vitamin C were in vigorous health throughout the experiment and displayed no clinical signs of vitamin C deficiency.

EXAMPLE VII

The 2-polyphosphorylation of ascorbic acid was conducted as described in Example I, except 1.0M L-ascorbic acid (initial concentration) was reacted with 2.0M sodium hexametaphosphate at 75°–80° C. and pH 11.5–12.0. After a 2 hr. reaction period, 42% unreacted L-ascorbate (iodine titration) was found and 49% 2-phosphorylation (uv analysis). Thus, about 10% of the starting L-ascorbate is unaccounted for, which indicates some destruction of the starting material at the high pH and temperature of the reaction.

Thin-layer chromatography (tlc) of the reaction mixture was done using a flexible film coated with cellulose. After spotting the reaction mixture on the chromatographic film, the chromatogram was developed using 30:35:15:20:0.4:5 (v/v/v/v/v/w) of water, ethanol, isobutanol, isopropanol, concentrated ammonium hydroxide and trichloroacetic acid. Upon spraying the dried chromatogram with an ethanolic solution of ferric chloride (1%), the reaction mixture gave six pink-colored components. The most intense spots appeared to have mobility equal to those of the 2-mono,2-di-, and 2-triphosphate esters of L-ascorbate. The higher phosphate esters of L-ascorbate gave faint pink spots.

We claim:

1. Ascorbate 2-polyphosphate compounds having the following formula:

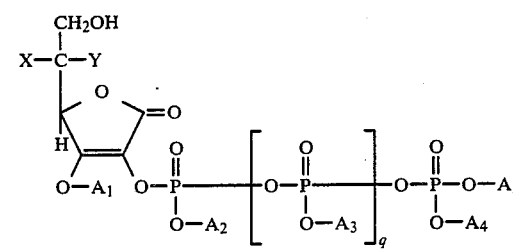

wherein X and Y are different and are respectively taken from the group consisting of —H and —OH, q ranges from 1 to 4, and A$_1$, A$_2$, A$_3$, A$_4$ and A$_5$ are respectively taken from the group consisting of hydrogen and salt-forming cations.

2. A new composition of matter which is ascorbate 2-triphosphate.

3. A method of synthesizing ascorbate 2-polyphosphate compounds which comprises the steps of:
   forming a reaction mixture comprising respective quantities of: (1) ascorbic acid or a derivative thereof, (2) a soluble salt of metaphosphoric acid, (3) water, and (4) sufficient base to give the mixture a pH of at least about 9; and
   allowing the mixture to react to form ascorbate 2-polyphosphate, and, during said reaction, maintaining the pH of the reaction mixture at a level of at least about 9.

4. The method of claim 3, said reactant (1) being selected from the group consisting of ascorbic acid, the alkali and tertiary amine salts of ascorbic acid, and derivatives of ascorbic acid having a C$_6$ base-stable blocking group thereon.

5. The method of claim 4, said reactant (1) being selected from the group consisting of the four stereoisomers of the compound of the formula

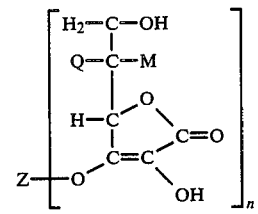

where Z is selected from the group consisting of hydrogen, the alkali metals, the alkaline earth metals and the tertiary amines, n is the valence of Z, and Q and M are different and taken from the group consisting of —H and —OH, and compounds of the formula

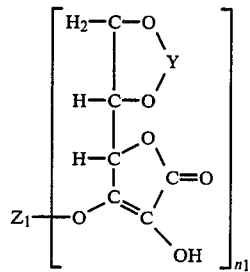

wherein $Z_1$ is selected from the group consisting of hydrogen, the alkali metals, alkaline earth metals and the tertiary amines, $n_1$ is the valence of $Z_1$ and Y represents cycloalkyls having from 5 to 7 carbon atoms or a group of the formula

where $R_1$ represents hydrogen, phenyl, furfural or alkyl groups of from 1 to 4 carbon atoms, and $R_2$ represents hydrogen or alkyl groups of from 1 to 4 carbon atoms.

6. The method of claim 3, said reactant (2) being selected from the group consisting of sodium and potassium trimetaphosphate.

7. The method of claim 3, said pH being maintained at a level of from about 9 to 13.

8. The method of claim 7, said pH level being from about 10 to 12.5.

9. The method of claim 8, said pH level being from about 11 to 12.

10. The method of claim 3, said reaction being carried out at a temperature of from about 20° to 80° C.

11. The method of claim 10, said temperature being from about 30° to 50° C.

12. The method of claim 3, said reaction being allowed to proceed for a period of from about 1 to 24 hours.

13. The method of claim 12, said period being from about 1 to 12 hours.

14. The method of claim 3, the concentration of said reactant (1) being from about 0.5 to 4 molar in said reaction mixture, with the molar ratio of said reactant (2) to said reactant (1) being from about 1.5 to 3.

15. The method of claim 14, the concentration of said first reactant being from about 0.75 to 1.5 molar.

16. The method of claim 3, including the step of adjusting the pH of said reaction mixture by addition of acid thereto after said reaction is completed.

17. The method of claim 16, said acid being an edible mineral or organic acid.

18. The method of claim 16, said acid being added to lower the pH of the reaction mixture to about 7.

19. The method of claim 3, including the step of recovering ascorbate 2-polyphosphate from said reaction mixture.

20. The method of claim 19, said recovery step comprising the steps of passing the reaction mixture through an ion-exchange column, and recovering a salt of ascorbate 2-polyphosphate.

21. The method of claim 3, including the step of treating said ascorbate 2-polyphosphate with acid to form preferentially L-ascorbate 2-phosphate.

* * * * *